(12) United States Patent
Chinta et al.

(10) Patent No.: US 8,318,999 B2
(45) Date of Patent: *Nov. 27, 2012

(54) METHOD OF COUPLING A CARBON SOURCE WITH TOLUENE TO FORM A STYRENE ETHYLBENZENE

(75) Inventors: Sivadinarayana Chinta, Missouri City, TX (US); Joseph Thorman, Houston, TX (US); James Butler, League City, TX (US)

(73) Assignee: Fina Technology Inc., Houston, TX (US)

( * ) Notice: Subject to any disclaimer, the term of this patent is extended or adjusted under 35 U.S.C. 154(b) by 107 days.

This patent is subject to a terminal disclaimer.

(21) Appl. No.: 12/763,234

(22) Filed: Apr. 20, 2010

(65) Prior Publication Data

US 2011/0257450 A1 Oct. 20, 2011

(51) Int. Cl.
*C07C 1/24* (2006.01)
(52) U.S. Cl. .......................... 585/323; 585/467; 585/469
(58) Field of Classification Search .................. 585/469, 585/467, 323
See application file for complete search history.

(56) References Cited

U.S. PATENT DOCUMENTS

| 2,519,788 | A | * | 8/1950 | Payne | 568/473 |
|---|---|---|---|---|---|
| 4,115,424 | A | | 9/1978 | Unland et al. | |
| 4,140,726 | A | * | 2/1979 | Unland et al. | 585/438 |
| 4,479,024 | A | * | 10/1984 | Bruylants et al. | 585/437 |
| 4,499,318 | A | | 2/1985 | Liu | |
| 6,025,293 | A | | 2/2000 | Wu et al. | |
| 2010/0041931 | A1 | | 2/2010 | Pelati et al. | |
| 2010/0168259 | A1 | | 7/2010 | Xiao et al. | |

OTHER PUBLICATIONS

Wieland, W.S., et al.; "Solid Base Catalysts for Side-Chain Alkylation of Toluene With Methanol"; Catalysts Today, 28, 1996, pp. 443-450.
Yashima, Tatsuaki, et al.; "Alkylation on Synthetic Zeolites III. Alkylation of Toluene with Methanol and Formaldehyde on Alkali Cation Exchanged Zeolites"; Journal of Catalysts, vol. 26, Issue 3, Sep. 1972; pp. 303-312.
B. Kumari Vasanthy et al., Applied Catalysis A: General, vol. 138 (1996) p. 51-61.

\* cited by examiner

*Primary Examiner* — Thuan D Dang

(57) ABSTRACT

A process is disclosed for making styrene or ethylbenzene by reacting toluene with a C1 source that is selected from the group consisting of methanol, formaldehyde, formalin, trioxane, methylformcel, paraformaldehyde, methylal, and combinations thereof.

12 Claims, 2 Drawing Sheets ical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

METHOD OF COUPLING A CARBON SOURCE WITH TOLUENE TO FORM A STYRENE ETHYLBENZENE

CROSS-REFERENCE TO RELATED APPLICATIONS

The present invention is related to co-pending application entitled Alkylation of Toluene to form Styrene and Ethylbenzene filed by Fina Technology, Inc. on the same date as this filing.

FIELD

The present invention relates to a method for the production of styrene and ethylbenzene. More specifically, the invention relates to the alkylation of toluene with a carbon source (herein referred to as a C1 source) such as methanol and/or formaldehyde, to produce styrene and ethylbenzene.

BACKGROUND

Styrene is an important monomer used in the manufacture of many plastics. Styrene is commonly produced by making ethylbenzene, which is then dehydrogenated to produce styrene. Ethylbenzene is typically formed by one or more aromatic conversion processes involving the alkylation of benzene.

Aromatic conversion processes, which are typically carried out utilizing a molecular sieve type catalyst, are well known in the chemical processing industry. Such aromatic conversion processes include the alkylation of aromatic compounds such as benzene with ethylene to produce alkyl aromatics such as ethylbenzene. Typically an alkylation reactor, which can produce a mixture of monoalkyl and polyalkyl benzenes, will be coupled with a transalkylation reactor for the conversion of polyalkyl benzenes to monoalkyl benzenes. The transalkylation process is operated under conditions to cause disproportionation of the polyalkylated aromatic fraction, which can produce a product having an enhanced ethylbenzene content and reduced polyalkylated content. When both alkylation and transalkylation processes are used, two separate reactors, each with its own catalyst, can be employed for each of the processes.

Ethylene is obtained predominantly from the thermal cracking of hydrocarbons, such as ethane, propane, butane, or naphtha. Ethylene can also be produced and recovered from various refinery processes. Thermal cracking and separation technologies for the production of relatively pure ethylene can account for a significant portion of the total ethylbenzene production costs.

Benzene can be obtained from the hydrodealkylation of toluene that involves heating a mixture of toluene with excess hydrogen to elevated temperatures (for example 500° C. to 600° C.) in the presence of a catalyst. Under these conditions, toluene can undergo dealkylation according to the chemical equation: $C_6H_5CH_3 + H_2 \rightarrow C_6H_6 + CH_4$. This reaction requires energy input and as can be seen from the above equation, produces methane as a byproduct, which is typically separated and may used as heating fuel for the process.

Another known process includes the alkylation of toluene to produce styrene and ethylbenzene. In this alkylation process, various aluminosilicate catalysts are utilized to react methanol and toluene to produce styrene and ethylbenzene. However, such processes have been characterized by having very low yields in addition to having very low selectivity to styrene and ethylbenzene.

In view of the above, it would be desirable to have a process of producing styrene and/or ethylbenzene that does not rely on thermal crackers and expensive separation technologies as a source of ethylene. It would further be desirable to avoid the process of converting toluene to benzene with its inherent expense and loss of a carbon atom to form methane. It would be desirable to produce styrene without the use of benzene and ethylene as feedstreams. It would also be desirable to produce styrene and/or ethylbenzene in one reactor without the need for separate reactors requiring additional separation steps. Furthermore, it is desirable to achieve a process having a high yield and selectivity to styrene and ethylbenzene.

SUMMARY

An embodiment of the present invention is a process for making styrene and ethylbenzene by providing a C1 source that includes either methanol or formaldehyde to a reactor and reacting the C1 source with toluene to form a product stream comprising styrene and/or ethylbenzene.

Another embodiment of the present invention is a process for making styrene by converting methanol to formaldehyde and coupling methanol and/or formaldehyde with toluene in one or more reactors to form a product stream comprising styrene and/or ethylbenzene. The product stream can also include hydrogen, water, or methanol. Any unreacted methanol can be separated from the product stream and then recycled to the one or more reactors.

The process may include utilizing one or more reactors including an oxidation reaction zone to convert methanol into formaldehyde and water. The process can optionally include utilizing one or more reactors including a dehydrogenation reaction zone to convert methanol into formaldehyde and hydrogen. The one or more reactors can also comprise a reaction zone under reaction conditions containing a catalyst for reacting toluene and formaldehyde to form styrene or ethylbenzene. The catalyst can be an acidic, basic or neutral catalyst, and can be an acidic, basic or neutral zeolite catalyst. The catalyst can comprise one or more promoters chosen from the group of alkali elements, alkaline earth elements, rare earth elements, Y, Zr, Nb, Co, Ga, P and B, and derivatives thereof.

The product stream can include toluene, water, methanol or formaldehyde. The unconverted feedstock can be separated from the product stream and then recycled to the one or more reactors. The one or more reactors can include a reaction zone under reaction conditions containing a catalyst for reacting toluene and formaldehyde to form styrene. The process can include passing the product stream to a separation stage for separating toluene, formaldehyde and methanol from the product stream. A stream containing toluene, formaldehyde and methanol may be obtained from the separation stage and recycled to the one or more reactors. The separation stage can include a membrane separation capable of removing hydrogen from the stream containing toluene, formaldehyde and methanol.

An aspect of the invention includes feeding toluene and a C1 source to one or more reactors. The toluene and C1 source are reacted in the one or more reactors to form a product stream comprising one or more of styrene, ethylbenzene, toluene, water, or formaldehyde. The product stream then passes to a separation stage for separating styrene and ethylbenzene from the second product stream. Toluene, C1 source and formaldehyde, if present, can be separated from the product stream and recycled to the one or more reactors.

DETAILED DESCRIPTION

In an aspect of the current invention, toluene is reacted with a carbon source capable of coupling with toluene to form ethylbenzene or styrene, which can be referred to as a C1 source, to produce styrene and ethylbenzene. In an embodiment, the C1 source includes methanol or formaldehyde or a mixture of the two. In an alternative embodiment, toluene is reacted with one or more of the following: Formalin, Trioxane, Methylformcel, Paraformaldehyde and Methylal. In a further embodiment, the C1 source is selected from the group consisting of methanol, formaldehyde, Formalin (37-50% $H_2CO$ in solution of water and MeOH), Trioxane (1,3,5-trioxane), Methylformcel (55% $H_2CO$ in methanol), Paraformaldehyde and Methylal (dimethoxymethane), and combinations thereof.

Formaldehyde can be produced either by the oxidation or dehydrogenation of methanol.

In an embodiment, formaldehyde is produced by the dehydrogenation of methanol to produce formaldehyde and hydrogen gas. This reaction step produces a dry formaldehyde stream that may be preferred, as it would not require the separation of the water prior to the reaction of the formaldehyde with toluene. The dehydrogenation process is described in the equation below:

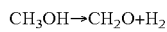
$$CH_3OH \rightarrow CH_2O + H_2$$

Formaldehyde can also be produced by the oxidation of methanol to produce formaldehyde and water. The oxidation of methanol is described in the equation below:

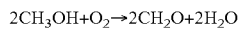
$$2CH_3OH + O_2 \rightarrow 2CH_2O + 2H_2O$$

In the case of using a separate process to obtain formaldehyde, a separation unit may then be used in order to separate the formaldehyde from the hydrogen gas or water from the formaldehyde and unreacted methanol prior to reacting the formaldehyde with toluene for the production of styrene. This separation would inhibit the hydrogenation of the formaldehyde back to methanol. Purified formaldehyde could then be sent to a styrene reactor and the unreacted methanol could be recycled.

Although the reaction has a 1:1 molar ratio of toluene and the C1 source, the ratio of the feedstreams is not limited within the present invention and can vary depending on operating conditions and the efficiency of the reaction system. If excess toluene or C1 source is fed to the reaction zone, the unreacted portion can be subsequently separated and recycled back into the process. In one embodiment the ratio of toluene:C1 source can range from between 100:1 to 1:100. In alternate embodiments the ratio of toluene:C1 source can range between from 50:1 to 1:50; from 20:1 to 1:20; from 10:1 to 1:10; from 5:1 to 1:5; from 2:1 to 1:2.

Figure 1:
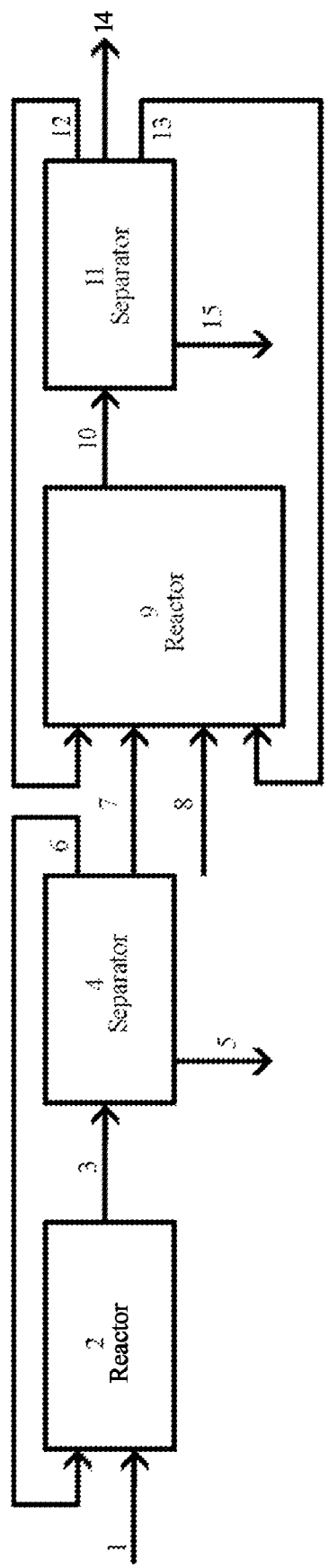
FIG. 1 illustrates a flow chart for the production of styrene by the reaction of formaldehyde and toluene, wherein the formaldehyde is first produced in a separate reactor by either the dehydrogenation or oxidation of methanol and is then reacted with toluene to produce styrene.

In FIG. 1 there is a simplified flow chart of one embodiment of the styrene production process described above. In this embodiment, a first reactor (2) is either a dehydrogenation reactor or an oxidation reactor. This reactor is designed to convert the first methanol feed (1) into formaldehyde. The gas product (3) of the reactor is then sent to a gas separation unit (4) where the formaldehyde is separated from any unreacted methanol and unwanted byproducts. Any unreacted methanol (6) can then be recycled back into the first reactor (2). The byproducts (5) are separated from the clean formaldehyde (7).

In one embodiment the first reactor (2) is a dehydrogenation reactor that produces formaldehyde and hydrogen and the separation unit (4) is a membrane capable of removing hydrogen from the product stream (3).

In an alternate embodiment the first reactor (2) is an oxidative reactor that produces product stream (3) comprising formaldehyde and water. The product stream (3) comprising formaldehyde and water can then be sent to the second reactor (9) without a separation unit (4).

The formaldehyde feed stream (7) is then reacted with a feed stream of toluene (8) in a second reactor (9). The toluene and formaldehyde react to produce styrene. The product (10) of the second reactor (9) may then be sent to an optional separation unit (11) where any unwanted byproducts (15) such as water can separated from the styrene, unreacted formaldehyde and unreacted toluene. Any unreacted formaldehyde (12) and the unreacted toluene (13) can be recycled back into the reactor (9). A styrene product stream (14) can be removed from the separation unit (11) and subjected to further treatment or processing if desired.

The operating conditions of the reactors and separators will be system specific and can vary depending on the feedstream composition and the composition of the product streams. The reactor (9) for the reaction of toluene and formaldehyde will operate at elevated temperatures and pressures and may contain a basic or neutral catalyst system. The temperature can range in a non-limiting example from 250° C. to 750° C., optionally from 300° C. to 500° C., optionally from 325° C. to 450° C. The pressure can range in a non-limiting example from 1 atm to 70 atm, optionally from 1 atm to 35 atm, optionally from 1 atm to 5 atm.

Figure 2:
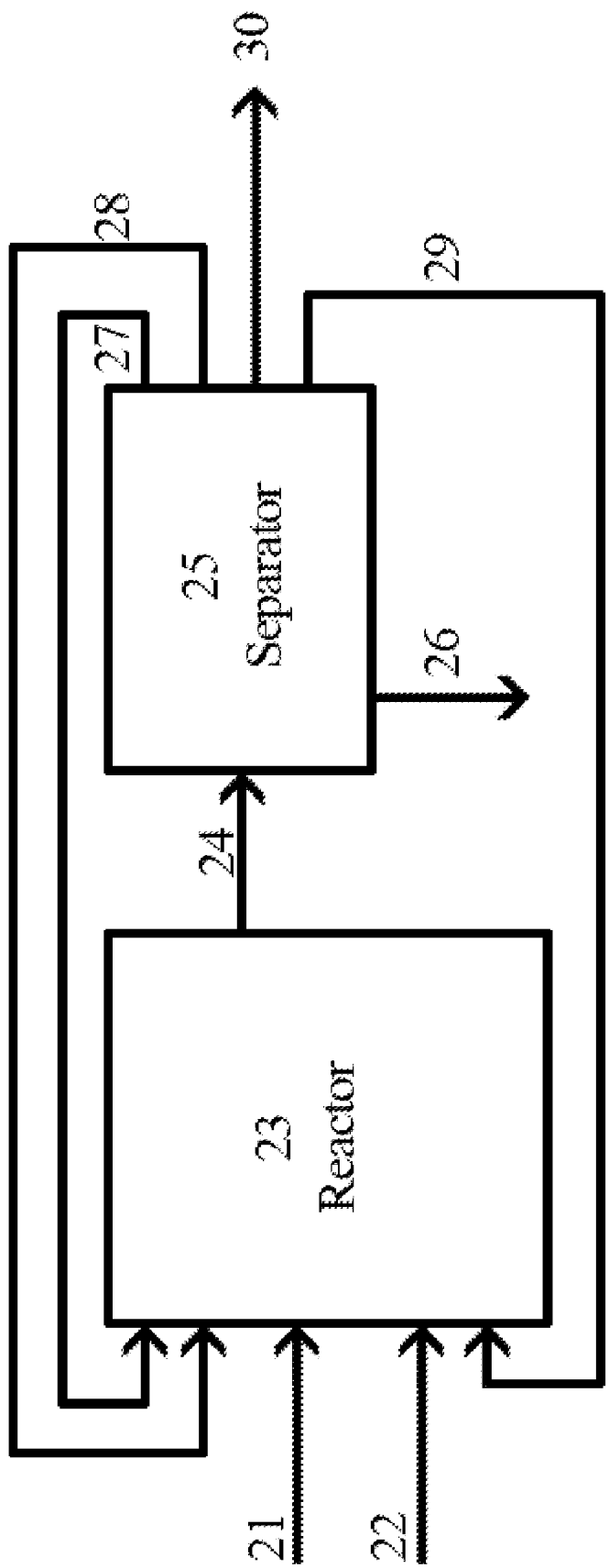
FIG. 2 illustrates a flow chart for the production of styrene by the reaction of formaldehyde and toluene, wherein methanol and toluene are fed into a reactor, wherein the methanol is converted to formaldehyde and the formaldehyde is reacted with toluene to produce styrene.

FIG. 2 is a simplified flow chart of another embodiment of the styrene process discussed above. A C1 source containing feed stream (21) is fed along with a feed stream of toluene (22) in a reactor (23). Toluene and the C1 source then react to produce styrene. The product (24) of the reactor (23) may then be sent to an optional separation unit (25) where any unwanted byproducts (26) can separated from the styrene, and any unreacted C1 source, unreacted methanol, unreacted formaldehyde and unreacted toluene. Any unreacted methanol (27), unreacted formaldehyde (28) and the unreacted toluene (29) can be recycled back into the reactor (23). A styrene product stream (30) can be removed from the separation unit (25) and subjected to further treatment or processing if desired.

The operating conditions of the reactors and separators will be system specific and can vary depending on the feedstream composition and the composition of the product streams. The reactor (23) for the reactions of methanol to formaldehyde and toluene with a C1 source, such as formaldehyde, will operate at elevated temperatures and pressures and may contain a basic or neutral catalyst system. The temperature can range in a non-limiting example from 250° C. to 750° C., optionally from 300° C. to 500° C., optionally from 325° C. to 450° C. The pressure can range in a non-limiting example from 1 atm to 70 atm, optionally from 1 atm to 35 atm, optionally from 1 atm to 5 atm.

Improvement in side chain alkylation selectivity may be achieved by treating a molecular sieve zeolite catalyst with chemical compounds to inhibit the external acidic sites and minimize aromatic alkylation on the ring positions. Another means of improvement of side chain alkylation selectivity can be to inhibit overly basic sites, such as for example with the addition of a boron compound. Another means of improvement of side chain alkylation selectivity can be to impose restrictions on the catalyst structure to facilitate side chain alkylation. In one embodiment the catalyst used in an embodiment of the present invention is a basic or neutral catalyst.

The catalytic reaction systems suitable for this invention can include one or more of the zeolite or amorphous materials modified for side chain alkylation selectivity. A non-limiting example can be a zeolite promoted with one or more of the following: Ru, Rh, Ni, Co, Pd, Pt, Mn, Ti, Zr, V, Nb, K, Cs, Ga, B, P or Na. In an embodiment, the zeolite can be promoted with one or more of Cs, B, Co, or Ga. In general the promoter exchanges with Na within the zeolite or amorphous material. Promoter can also be attached to the zeolite or amorphous material in an occluded manner. In an aspect the amount of promoter is determined by the amount needed to yield less than 0.5 mol % of ring alkylated products such as xylenes from a coupling reaction of toluene and a C1 source.

Zeolite materials suitable for this invention may include silicate-based zeolites and amorphous compounds such as faujasites, mordenites, etc. Silicate-based zeolites are made of alternating $SiO_2$ and $MO_x$ tetrahedra, where M is an element selected from the Groups 1 through 16 of the Periodic Table (new IUPAC). These types of zeolites have 4-, 6-, 8-, 10-, or 12-membered oxygen ring channels. An example of zeolites of this invention can include faujasites. Other suitable zeolite materials include X-type and Y-type zeolites. In a more specific embodiment, the zeolite is an X-type zeolite.

The present catalyst is adaptable to use in the various physical forms in which catalysts are commonly used. The catalyst of the invention may be used as a particulate material in a contact bed or as a coating material on structures having a high surface area. If desired, the catalyst can be deposited with various catalyst binder and/or support materials.

A catalyst comprising a substrate that supports a promoting metal or a combination of metals can be used to catalyze the reaction of hydrocarbons. The method of preparing the catalyst, pretreatment of the catalyst, and reaction conditions can influence the conversion, selectivity, and yield of the reactions.

The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

The term "substrate" as used herein is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%. If more than one promoters are combined, they together generally can range from 0.01% up to 70% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can include an alumina or aluminate framework as a support. Upon calcination these elements can be altered, such as through oxidation which would increase the relative content of oxygen within the final catalyst structure. The combination of the catalyst of the present invention combined with additional elements such as a binder, extrusion aid, structured material, or other additives, and their respective calcination products, are included within the scope of the invention.

In one embodiment, the catalyst can be prepared by combining a substrate with at least one promoter element. Embodiments of a substrate can be a molecular sieve, from either natural or synthetic sources. Zeolites and zeolite-like materials can be an effective substrate. Alternate molecular sieves also contemplated are zeolite-like materials the crystalline silicoaluminophosphates (SAPO) and the aluminophosphates (ALPO).

The present invention is not limited by the method of catalyst preparation, and all suitable methods should be considered to fall within the scope herein. Particularly effective techniques are those utilized for the preparation of solid catalysts. Conventional methods include co-precipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

When slurries, precipitates or the like are prepared, they will generally be dried, usually at a temperature sufficient to volatilize the water or other carrier, such as from 100° C. to 250° C., with or without vacuum. Irrespective of how the components are combined and irrespective of the source of the components, the dried composition is generally calcined in the presence of a free oxygen-containing gas, usually at temperatures between about 300° C. and about 900° C. for from 1 to 24 hours. The calcination can be in an oxygen-containing atmosphere, or alternately in a reducing or inert atmosphere.

The prepared catalyst can be ground, pressed, sieved, shaped and/or otherwise processed into a form suitable for loading into a reactor. The reactor can be any type known in the art to make catalyst particles, such as a fixed bed, fluidized bed, or swing bed reactor. Optionally an inert material, such as quartz chips, can be used to support the catalyst bed and to place the catalyst within the bed. Depending on the catalyst, a pretreatment of the catalyst may, or may not, be necessary. For the pretreatment, the reactor can be heated to elevated temperatures, such as 200° C. to 900° C. with an air flow, such as 100 mL/min, and held at these conditions for a length of time, such as 1 to 3 hours. Then, the reactor can be brought to the operating temperature of the reactor, for example 300° C. to 550° C., or optionally down to atmospheric or other desired temperature. The reactor can be kept under an inert purge, such as under a nitrogen or helium purge.

Embodiments of reactors that can be used with the present invention can include, by non-limiting examples: fixed bed reactors; fluid bed reactors; and entrained bed reactors. Reactors capable of the elevated temperature and pressure as described herein, and capable of enabling contact of the reactants with the catalyst, can be considered within the scope of the present invention. Embodiments of the particular reactor system may be determined based on the particular design conditions and throughput, as by one of ordinary skill in the art, and are not meant to be limiting on the scope of the present invention. An example of a suitable reactor can be a fluid bed reactor having catalyst regeneration capabilities. This type of reactor system employing a riser can be modified as needed, for example by insulating or heating the riser if thermal input is needed, or by jacketing the riser with cooling water if thermal dissipation is required. These designs can also be used to replace catalyst while the process is in operation, by withdrawing catalyst from the regeneration vessel from an exit line or adding new catalyst into the system while in operation.

In another aspect, the one or more reactors may include one or more catalyst beds. In the event of multiple beds, an inert material layer can separate each bed. The inert material can comprise any type of inert substance, including quartz. In an embodiment, a reactor includes between 1 and 10 catalyst beds. In a further embodiment, a reactor includes between 2 and 5 catalyst beds. In addition, the C1 source and toluene may be injected into a catalyst bed, an inert material layer, or both. In a further embodiment, at least a portion of the C1 source is injected into a catalyst bed(s) and at least a portion of the toluene feed is injected into an inert material layer(s).

In an alternate embodiment, the entire C1 source is injected into a catalyst bed(s) and all of the toluene feed is injected into an inert material layer(s). In another aspect, at least a portion of the toluene feed is injected into a catalyst bed(s) and at least a portion the C1 source is injected into an inert material layer(s). In a further aspect, all of the toluene feed is injected into a catalyst bed(s) and the entire C1 source is injected into an inert material layer(s).

The toluene and C1 source coupling reaction may have a toluene conversion percent greater than 0.01 mol %. In an embodiment the toluene and C1 source coupling reaction is capable of having a toluene conversion percent in the range of from 0.05 mol % to 40 mol %. In a further embodiment the toluene and C1 source coupling reaction is capable of having a toluene conversion in the range of from 2 mol % to 40 mol %, optionally from 5 mol % to 35 mol %, optionally from 20 mol % to 30 mol %.

In an aspect the toluene and C1 source coupling reaction is capable of selectivity to styrene greater than 1 mol %, relative to toluene. In another aspect, the toluene and C1 source coupling reaction is capable of selectivity to styrene in the range of from 1 mol % to 99 mol %. In an aspect the toluene to a C1 source coupling reaction is capable of selectivity to ethylbenzene greater than 1 mol %. In another aspect, the toluene and C1 source coupling reaction is capable of selectivity to ethylbenzene in the range of from 1 mol % to 99 mol %. In an aspect the toluene and C1 source coupling reaction is capable of yielding less than 0.5 mol % of ring alkylated products such as xylenes.

EXAMPLES

Example 1

Procedure used to produce the cesium ion-exchanged zeolite material: A glass cylinder (2" inside diameter), fitted with a sintered glass disk and stopcock at the lower end, was charged with 544-HP zeolite (100 g, W.R. Grace) and CsOH (400 mL, 1.0 M in water). The mixture was then brought to 90° C. and allowed to stand for 4 h. The liquid was drained from the zeolite material and another aliquot of CsOH (400 mL of 1.0 M solution in water) was added and allowed to stand for 3 hours at 90° C. The liquid was drained from the zeolite material and another aliquot of CsOH (400 mL of 1.0 M solution in water) was added and allowed to stand for 15 hours at 90° C. The liquid was drained from the zeolite material and dried at 150° C. for 1.5 hours.

Incipient wetness impregnation of $Ga(NO_3)_3$ on to the cesium ion-exchanged X-zeolite material: The cesium ion-exchanged zeolite material (50 g) was subjected to incipient wetness impregnation of $Ga(NO_3)_3$ by adding the $Ga(NO_3)_3$ solution (1.83 g $Ga(NO_3)_3$ in 13.3 mL of water) to the zeolite while stirring. The (Cs, Ga)/X material was then dried at 150° C. for 12 hours.

Deposition of 1.4 wt % boron onto cesium ion-exchanged zeolite material: The cesium ion-exchanged zeolite material (35 g) was treated with a solution of boric acid (2.8 g) dissolved in acetone (500 mL) at room temperature for 2 hours. The (Cs, B)/X material was then dried at 110° C. for 20 hours.

Incipient wetness impregnation of $Co(NO_3)_2$ on to the cesium ion-exchanged X-zeolite material: The cesium ion-exchanged zeolite material (50 g) was subjected to incipient wetness impregnation of $Co(NO_3)_2$ by adding the $Co(NO_3)_2$ solution (2.46 g $Co(NO_3)_2$ in 13.3 mL of water) to the zeolite while stirring. The (Cs, Co)/X material was then dried at 150° C. for 12 hours.

Incipient wetness impregnation of $Co(NO_3)_2$ on to the cesium ion-exchanged L-zeolite material: The cesium ion-exchanged L-type zeolite material (56 g, ZD97021 from Zeolyst) was subjected to incipient wetness impregnation of $Co(NO_3)_2$ by adding the $Co(NO_3)_2$ solution (2.765 g $Co(NO_3)_2$ in 47.6 mL of water) to the zeolite while stirring. The (Cs, Co)/X material was then dried at 150° C. for 12 hours.

Stainless steel reactor details: A stainless steel tube with 0.5-inch outer diameter and 0.465 inch internal diameter was filled with crushed quartz of 850-2000 μm size (to a height of about 10 inches, 29.2 mL), then the catalyst (to a height of 3.0 inches; 6.6 mL, 3.35 g) at sizes ranging from 250-425 μm, and then more crushed quartz of 850-2000 μm size (to a height of about 17 inches, 37.2 mL) such that a 0.125 inch stainless steel thermowell was positioned in the middle of the catalyst bed.

Ceramic lined stainless steel reactor details: Experiments were carried out with methanol and toluene over the respective catalyst. A 0.75-inch outside diameter stainless steel tube was fitted with a 0.5-inch inside diameter ceramic liner. The tube was then filled with crushed quartz (to a height of about 13.5 inches), then the catalyst (see Table 1) at sizes ranging from 250-425 μm, and then more crushed quartz (of a height of about 17 inches) such that a silcosteel coated thermowell was positioned in the middle of the bed. The reactor was installed in a 3-zone furnace and heated to 500° C. and held for 2 hours while passing nitrogen through it at 150 cc/min. The reactor was then cooled to the reaction temperature of 420° C. The feed was comprised of toluene, methanol and nitrogen. The flow rates were corrected for temperature, the flow rate of gases at the reaction temperature is found in the table as well as the GHSV. The effluent was monitored by an on-line gas chromatograph.

The information in Table 1 describes the conditions used in testing various catalysts for producing styrene and ethylbenzene from toluene and methanol:

TABLE 1

| Catalyst | Reactor | Catalyst Size | MeOH (Liq) (mL/hr) | PhMe (Liq) (mL/hr) | $N_{2\ (carrier\ gas)}$ (cc/min) | Tol/MeOH (molar ratio) | Reaction Temp (C.) | Pressure psig | Contact Time (s) | Time on stream min |
|---|---|---|---|---|---|---|---|---|---|---|
| Cs/X | Ceramic Lined | 250-425 micron | 4.9 | 13.0 | 20 | 1.0 | 420 | 3.7 | 1.5 | 131 |
| Cs/X | SS | 2 mm | 2.3 | 23.0 | 20 | 3.7 | 420 | 5 | 4.1 | 123 |
| Cs, B/X | SS | 250-425 micron | 1.6 | 18.0 | 28 | 3.9 | 420 | 4 | 1.9 | 108 |
| Cs, B/X | SS | 250-425 micron | 5.4 | 14.0 | 28 | 1.0 | 420 | 5 | 1.6 | 243 |
| Cs, Co/X | Ceramic Lined | 250-425 micron | 1.5 | 16.9 | 28 | 4.3 | 420 | 2 | 1.6 | 131 |
| Cs, Co/X | Ceramic Lined | 250-425 micron | 4.9 | 13.0 | 28 | 1.0 | 420 | 4 | 1.5 | 196 |
| Cs, Ga/X | Ceramic Lined | 250-425 micron | 1.5 | 17.0 | 28 | 4.3 | 420 | 1.8 | 1.6 | 117 |
| Cs, Ga/X | Ceramic Lined | 250-425 micron | 4.9 | 13.0 | 28 | 1.0 | 420 | 2.6 | 1.4 | 318 |
| Cs/ZSM5 | SS | 250-425 micron | 2.3 | 23.0 | 20 | 3.7 | 420 | 9 | 5 | 99 |
| Cs/Y | SS | Extrudates | 0.8 | 9.0 | 10 | 4.1 | 425 | 1.8 | 2.6 | 180 |
| Cs/L | Ceramic Lined | 250-425 micron | 1.6 | 17.0 | 28 | 4.1 | 420 | 1.6 | 1.5 | 153 |
| Cs/L | Ceramic Lined | 250-425 micron | 4.9 | 13.0 | 28 | 1.0 | 420 | 2.2 | 1.4 | 254 |
| Cs, Co/L | Ceramic Lined | 250-425 micron | 1.6 | 17.0 | 28 | 4.1 | 420 | 1.6 | 1.5 | 140 |
| Cs, Co/L | Ceramic Lined | 250-425 micron | 4.9 | 13.0 | 28 | 1.0 | 420 | 2.2 | 1.4 | 267 |
| (Cs, 1.4 wt % B)/X | Ceramic Lined | 250-425 micron | 5 | 13 | 70 | 1.0 | 420 | 1.5 | 2.6 | 95 |

Table 2 shows the results of the experiments from Example #1. The X-zeolite based catalyst demonstrated a higher toluene conversion and high EB selectivity over the comparable other zeolite based catalysts. The (Cs, Ga)/X catalyst demonstrated a higher toluene conversion than the Cs/X and (Cs, B)/X catalysts:

TABLE 2

| Catalyst | $X_{Tol}$ wt % | $S_{EB}$ mol % | $S_{Sty}$ mol % | $S_{Bz}$ mol % | $S_{Xyl}$ mol % |
|---|---|---|---|---|---|
| Cs/X | 7.2 | 83.6 | 8.2 | 0.25 | 0.0 |
| Cs/X | 7.5 | 82.2 | 8.7 | 1.4 | 0.5 |
| Cs, B/X | 10.0 | 80.3 | 11.2 | 0.9 | 0.0 |
| Cs, B/X | 11.5 | 77.5 | 14.2 | 0.4 | 0.0 |
| Cs, Co/X | 9.0 | 87.6 | 4.1 | 2.5 | 0.0 |
| Cs, Co/X | 12.0 | 87.5 | 3.5. | 3.2 | 0.0 |
| Cs, Ga/X | 3.8 | 90.9 | 2.3 | 1.0 | 0.0 |
| Cs, Ga/X | 14.6 | 89.1 | 4.4 | 0.4 | 0.0 |
| Cs/ZSM-5 | 0.4 | 83.3 | 6.5 | 2.5 | 2.1 |
| Cs/Y | 0.1 | 13.9 | 43.2 | 51.2 | 0.0 |
| Cs/L | 1.0 | 11.1 | 19.7 | 0.0 | 0.0 |
| Cs/L | 0.5 | 20.9 | 57.6 | 8.5 | 0.0 |
| Cs, Co/L | 0.5 | 43.3 | 44.1 | 5.1 | 0.0 |
| Cs, Co/L | 0.5 | 19.2 | 52.8 | 7.7 | 0.0 |
| (Cs, 1.4 wt % B)/X | 18.7 | 81.0 | 16.2 | 0.5 | 0.1 |

Example 2

Another experiment was carried out with 1,3,5-trioxane and toluene over Cs/X and (Cs, B)/X catalysts. A 0.75-inch diameter stainless steel tube was fitted with a 0.5-inch inside diameter ceramic liner. The tube was then filled with crushed quartz (to a height of about 6 inches) such that a silcosteel coated thermowell was positioned in the middle of the bed. The reactor was installed in a 3-zone furnace and heated to 500° C. for 6 hours while passing nitrogen through the reactor at 150 cc/min. The reactor was then cooled to the reaction temperature. The feed contained 1,3,5-trioxane dissolved in toluene (see Table 3) and nitrogen (28 cc/min). The effluent was monitored by an on-line gas chromatograph.

The Cs/X catalyst was made by the following procedure: A glass cylinder (2" inside diameter), fitted with a sintered glass disk and stopcock at the lower end, was charged with 544-HP zeolite (100 g, W.C. Grace) and CsOH (400 mL, 1.0 M in water). The mixture was then brought to 90° C. and allowed to stand for 4 h. The liquid was drained from the zeolite material and another aliquot of CsOH (400 mL of 1.0 M solution in water) was added and allowed to stand for 3 hours at 90° C. The liquid was drained from the zeolite material and another aliquot of CsOH (400 mL of 1.0 M solution in water) was added and allowed to stand for 15 hours at 90° C. The liquid was drained from the zeolite material and dried at 150° C. for 1.5 hours.

The (Cs, B)/X catalyst was prepared by deposition of 1.4 wt % boron onto cesium ion-exchanged zeolite material: The cesium ion-exchanged zeolite material (35 g) was treated with a solution of boric acid (2.8 g) dissolved in acetone (500 mL) at room temperature for 2 hours. The (Cs, B)/X material was then dried at 110° C. for 20 hours.

The information in Table 3 describes the conditions used in testing various catalysts for producing styrene and ethylbenzene from toluene and methanol:

TABLE 3

| Catalyst | Catalyst (g) | Reaction Temp (° C.) | mol % trioxane in toluene | Flow rate of toluene + trioxane (cc/h) | Nitrogen (cc/min) | WHSV (1/h) | Contact time (s) |
|---|---|---|---|---|---|---|---|
| Cs/X | 11.4 | 425 | 10 | 7 | 28 | 0.5 | 5.0 |
|  |  | 425 | 10 | 26 | 28 | 1.8 | 2.1 |
| Cs/X | 11.4 | 425 | 22 | 6 | 28 | 0.4 | 5.0 |
|  |  | 425 | 22 | 25 | 28 | 1.7 | 2.0 |
| Cs/X | 11.8 | 375 | 10 | 8 | 28 | 0.5 | 5.1 |
|  |  | 375 | 10 | 31 | 28 | 1.9 | 2.0 |
| (Cs, B)/X | 11.2 | 425 | 10 | 7 | 28 | 0.5 | 5.0 |
|  |  | 425 | 10 | 26 | 28 | 1.7 | 2.1 |
| (Cs, B)/X | 11.1 | 375 | 10 | 8 | 28 | 0.5 | 5.0 |
|  |  | 375 | 10 | 31 | 28 | 1.9 | 2.1 |

Table 4 shows the results of the experiments (all conversions are shown in mole %, not weight %), which demonstrate better toluene conversion and selectivities to desired products than achieved in prior literature:

TABLE 4

| Catalyst | $X_{Tol}$ wt % | $S_{Sty}$ mol % | $S_{EB}$ mol % | $S_{Cumene}$ mol % | $S_{Xyl}$ mol % |
|---|---|---|---|---|---|
| Cs/X | 4.6 | 9.1 | 68.3 | 6.2 | 0 |
| Cs/X | 2.6 | 5.5 | 80.3 | 3.9 | 0 |
| Cs/X | 7.2 | 1.8 | 85.6 | 3.6 | 0 |
| Cs/X | 6.5 | 12.7 | 75.4 | 3.7 | 0 |
| Cs/X | 5.0 | 19.9 | 63.2 | 8.2 | 0 |
| Cs/X | 3.8 | 57.2 | 29.2 | 6.1 | 0 |
| (Cs, B)/X | 5.2 | 3.3 | 86.6 | 1.4 | 0 |
| (Cs, B)/X | 4.5 | 21.3 | 87.5 | 2.4 | 0 |
| (Cs, B)/X | 4.9 | 15.4 | 70.9 | 4.7 | 0 |
| (Cs, B)/X | 5.7 | 62.2 | 30.0 | 2.9 | 0 |

The term "conversion" refers to the percentage of reactant (e.g. toluene) that undergoes a chemical reaction.

$X_{Tol}$=conversion of toluene(mol %)=(Tol$_{in}$−Tol$_{out}$)/ Tol$_{in}$ $X_{MeOH}$=conversion of methanol to styrene+ethylbenzene(mol %)

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "selectivity" refers to the relative activity of a catalyst in reference to a particular compound in a mixture. Selectivity is quantified as the proportion of a particular product relative to all other products.

$S_{Sty}$=selectivity of toluene to styrene(mol %)=Sty$_{out}$/ Tol$_{converted}$ $S_{Bz}$=selectivity of toluene to benzene(mol %)=Benzene$_{out}$/Tol$_{converted}$ $S_{EB}$=selectivity of toluene to ethylbenzene (mol %)=EB$_{out}$/Tol$_{converted}$ $S_{Xyl}$=selectivity of toluene to xylenes(mol %)=Xylenes$_{out}$/Tol$_{converted}$ $S_{sty+EB}$(MeOH)=selectivity of methanol to styrene+ ethylbenzene(mol %)=(Sty$_{out}$+EB$_{out}$)/ MeOH$_{converted}$ The term "spent catalyst" refers to a catalyst that has lost enough catalyst activity to no longer be efficient in a specified process. Such efficiency is determined by individual process parameters.

The term "zeolite" refers to a molecular sieve containing an aluminosilicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves. An X-zeolite is defined as having a Si/Al molar ratio between 1.0 and 2.0. A Y-zeolite is defined as having a Si/Al molar ratio greater than 2.0.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A process for making styrene comprising:
   providing a C1 source to a reactor, wherein the C1 source comprises a methanol fraction;
   converting the methanol fraction of the C1 source using a catalyst comprising a X zeolite, cesium and a component selected from the group consisting of gallium, boron, and cobalt to form an intermediate product comprising formaldehyde; and
   reacting toluene with the formaldehyde in the reactor containing said catalyst to form a product stream comprising ethylbenzene and styrene, wherein the ratio of toluene to intermediate product source is between 5:1 to 1:5.

2. The process of claim 1, wherein the ratio of toluene to intermediate product is between 2:1 to 1:2.

3. The process of claim 2, wherein toluene conversion is greater than 0.1 mol %.

4. The process of claim 1, wherein selectivity to styrene is greater than 2 mol % and selectivity to ethylbenzene is greater than 30 mol %.

5. The process of claim 1, wherein the reactor comprises multiple catalyst beds, wherein each catalyst bed is separated by an inert layer.

6. The process of claim 1, further comprising:
   utilizing a preliminary reactor with a reaction zone under reaction conditions containing a catalyst to convert at least a portion of the C1 source fraction that is methanol to form the intermediate product comprising formaldehyde;
   providing one or more components of the intermediate product to the reactor for reaction with toluene to form the product stream comprising ethylbenzene and styrene.

7. The process of claim 1, wherein the C1 source further comprises formaldehyde, formalin, trioxane, methylformcel, paraformaldehyde, methylal, or combinations thereof.

8. A process for making styrene and ethylbenzene comprising:
   providing a C1 source comprising methanol to one or more first reactors;
   reacting the methanol of the C1 source to form a first product stream comprising formaldehyde; and
   reacting toluene with the first product stream in one or more second reactors to form a product stream comprising styrene and ethylbenzene, wherein the ratio of toluene to first product stream is between 5:1 to 1:5; wherein the one or more second reactors comprises a catalyst comprising a X zeolite, cesium and a component selected from the group consisting of gallium, boron, and cobalt.

9. The process of claim 8, wherein the C1 source and toluene have a molar ratio of between 2:1 to 1:2 C1 source to toluene.

10. The process of claim 8, wherein toluene conversion is greater than 0.1 mol %.

11. The process of claim 8, wherein selectivity to styrene is greater than 2 mol % and selectivity to ethylbenzene is greater than 30 mol %.

12. The process of claim 8, wherein the C1 source further comprises formaldehyde, formalin, trioxane, methylformcel, paraformaldehyde, methylal, or combinations thereof.

* * * * *